(12) United States Patent
Britzen (10) Patent No.: US 10,497,115 B2
(45) Date of Patent: Dec. 3, 2019

(54) METHOD, APPARATUS AND COMPUTER PROGRAM FOR VISUALLY SUPPORTING A PRACTITIONER WITH THE TREATMENT OF A TARGET AREA OF A PATIENT

(71) Applicant: SIEMENS HEALTHCARE GMBH, Erlangen (DE)

(72) Inventor: Stefan Britzen, Buckenhof (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/332,085

(22) Filed: Oct. 24, 2016

(65) Prior Publication Data
US 2017/0116732 A1    Apr. 27, 2017

(30) Foreign Application Priority Data
Oct. 23, 2015    (DE) .......................... 10 2015 220 768

(51) Int. Cl.
*A61B 6/00*    (2006.01)
*A61B 6/12*    (2006.01)
(Continued)

(52) U.S. Cl.
CPC ............ *G06T 7/0012* (2013.01); *A61B 6/463* (2013.01); *A61B 6/504* (2013.01); *A61B 6/5211* (2013.01); *G06T 7/11* (2017.01); *A61B 6/12* (2013.01); *A61B 6/4441* (2013.01); *A61B 6/469* (2013.01); *A61B 6/481* (2013.01); *A61B 6/5235* (2013.01); *G06T 2207/10012* (2013.01);
(Continued)

(58) Field of Classification Search
None
See application file for complete search history.

(56) References Cited

U.S. PATENT DOCUMENTS 7,953,266 B2    5/2011    Gulsun et al.
8,073,227 B2 *  12/2011   Gulsun .................... G06T 7/60
                                                        382/131
(Continued)

OTHER PUBLICATIONS

Andreas Grünauer, "Coronary Artery Tracking with Rule-based Gap Closing," Thesis, Vienna University of Technology, 2011.*
(Continued)

*Primary Examiner* — Soo Shin
(74) *Attorney, Agent, or Firm* — Laurence Greenberg; Werner Stemer; Ralph Locher (57) ABSTRACT

A method for visually supporting a practitioner with the treatment of a target area, in particular a tumor, of a patient is performed by using a treatment agent to be introduced into the target area through at least one supply blood vessel using a medical instrument. A region of interest is defined which describes the target area and a safety region surrounding the region of interest at a first distance, in an image data record showing the target area. Then an expansion region is defined which surrounds the region of interest at a second distance which is smaller than the first distance. Blood vessels are segmented in the image data record in a segmentation region including at least the safety region without the expansion region. A support display is shown displaying the blood vessels, in particular together with image data of the image data record and/or the instrument.

17 Claims, 3 Drawing Sheets

(51) Int. Cl.
*G06T 7/00* (2017.01)
*G06T 7/11* (2017.01)

(52) U.S. Cl.
CPC ............... *G06T 2207/10116* (2013.01); *G06T 2207/30096* (2013.01); *G06T 2207/30101* (2013.01)

(56) References Cited

U.S. PATENT DOCUMENTS

| | | | |
|---|---|---|---|
| 2005/0207630 A1* | 9/2005 | Chan | A61B 6/466 382/131 |
| 2006/0062447 A1* | 3/2006 | Rinck | G06T 17/10 382/154 |
| 2006/0159322 A1* | 7/2006 | Rinck | A61B 6/504 382/128 |
| 2007/0083099 A1* | 4/2007 | Henderson | A61B 5/02007 600/407 |
| 2009/0208078 A1* | 8/2009 | Fritz | G06T 7/0012 382/130 |
| 2012/0236259 A1* | 9/2012 | Abramoff | A61B 3/12 351/206 |
| 2013/0094725 A1 | 4/2013 | Gulsun et al. | |

OTHER PUBLICATIONS

Andreas Grünauer, "Coronary Artery Tracking with Rule-based Gap Closing," Thesis, Vienna University of Technology, 2011 (Year: 2011).*

* cited by examiner

METHOD, APPARATUS AND COMPUTER PROGRAM FOR VISUALLY SUPPORTING A PRACTITIONER WITH THE TREATMENT OF A TARGET AREA OF A PATIENT

CROSS-REFERENCE TO RELATED APPLICATION

This application claims the priority, under 35 U.S.C. § 119, of German Patent Application DE 10 2015 220 768.4, filed Oct. 23, 2015; the prior application is herewith incorporated by reference in its entirety.

BACKGROUND OF THE INVENTION

Field of the Invention

The invention relates to a method, an apparatus and a computer program for visually supporting a practitioner with the treatment of a target area, in particular a tumor, of a patient by using a treatment agent to be introduced into the target area through at least one supply blood vessel by using a medical instrument, wherein a region of interest which describes the target area and a safety region which surrounds the region of interest at a first distance are defined in an image data record which shows the target area.

New treatment methods, particularly in tumor therapy, propose the local application of treatment agents, for instance medicines, radiopharmaceuticals, chemotherapeutics and the like, directly in the target area to be treated, in particular a tumor. To this end, a medical instrument is guided through the blood vessels of the patient as far as a supply vessel for the target area, where the treatment agent can be introduced into the blood stream and is transported to the target area. A catheter can be used in particular as a medical instrument. In most cases the treatment takes place with visual support, which means that image data records of the target area (and the anatomical region including the same) are recorded, in particular intraoperatively, in which the course of the blood vessels, the target region, and when the intervention is monitored, also ideally the medical instrument, can be identified. In that way by administering a contrast agent, angiography recordings can be recorded as an image data record, for instance, in which the blood vessels in the anatomical region including the target area can be clearly identified. A practitioner must now decide on the basis of the course of the blood vessels which at least one blood vessel is particularly suitable as a supply vessel for the target area and will expose surrounding tissue to the treatment agent as little as possible.

Highlighting aids and the like were already proposed in the prior art in order to further improve the visual support. Support software for radiology already frequently uses detection algorithms in that case, in order to be able to identify objects of interest in clinical image data records. In the presence of large structures, the visualization can be easily adapted by smoothing the shapes of the object. The problem is, however, complicated if there are many small structures, which may be important to the practitioner. One example of such small structures are the aforementioned supply vessels for navigation and treatment planning, for instance in so-called TACE treatment procedures (Transarterial chemoembolization).

Methods for the fully automatic detection of blood vessels in image data records, for instance the x-ray image data records used explicitly in that context, were already proposed in the prior art. Reference is made merely by way of example to U.S. Pat. No. 7,953,266 B2 and U.S. Pat. No. 8,073,227 B2, which address the modeling of vascular trees in digital medical images.

In concrete support of the local treatment of a target area, in particular a tumor, by using a treatment agent through supply vessels, to further support the practitioner it was already proposed to firstly automatically and/or manually define a region of interest (ROI) which describes the target area. In order to be able to determine all relevant blood vessels that may be suitable as supply vessels, provision can then be made to define a safety region at a first distance about the region of interest. Algorithms such as those cited by way of example can now detect blood vessels within the safety region about the region of interest. Those blood vessels are then continued as far as a reference point ("proximal point") in a supply blood vessel supplying the anatomical region in which the target area is located. A support display which can be generated therefrom shows the corresponding candidates for supply vessels, in particular it overlays image data of the image data record, so that an improved orientation is provided for the practitioner, particularly if the support display also shows the medical instrument during the navigation.

Since a large number of blood vessels are typically present in the safety region surrounding the region of interest, such a support display, in which detected blood vessels are additionally shown or highlighted, can quickly become confusing and unclear for a practitioner. It was thus proposed in that case only to display the blood vessels to be displayed from a specific size, which may, however, also be confusing for the person carrying out the treatment, since further blood vessels can be identified in the image data therefor, which are frequently also shown in the support display, in which it is unclear whether the blood vessel is merely not shown or was incorrectly not detected.

SUMMARY OF THE INVENTION

It is accordingly an object of the invention to provide a method, an apparatus and a computer program for visually supporting a practitioner with the treatment of a target area of a patient, which overcome the hereinafore-mentioned disadvantages of the heretofore-known methods, apparatuses and programs of this general type and which provide a possibility of generating an improved support display, which is completely, intuitively understandable and limited to the relevant information.

With the foregoing and other objects in view there is provided, in accordance with the invention, a method for visually supporting a practitioner with the treatment of a target area, in particular a tumor, of a patient by using a treatment agent to be introduced into the target area through at least one blood vessel supply by using a medical instrument, wherein after defining a region of interest which describes the target area and a safety region, which surrounds the region of interest at a first distance, in an image data record which shows the target area, the following steps are performed:

defining an expansion region, which surrounds the region of interest at a second distance which is less than the first distance, segmenting blood vessels in the image data record in a segmentation region including at least the safety region without the expansion region, and displaying a support display displaying the blood vessels, in particular together with image data of the image data record and/or the instrument.

The basis of the present invention is therefore an, in particular, three-dimensional image data record of the target area, in which the region of interest and the safety region can be defined manually and/or automatically. Such an image data record can be an x-ray image data record for instance, which was recorded after or during the administration of contrast agent. An x-ray device can be used to record the image data record, for instance. The x-ray device, for instance a C-arm x-ray device, also permits intraoperative or interventional image monitoring. Other modalities for recording the image data record are naturally also conceivable, for instance magnetic resonance. If only the region of interest and the safety region are defined, in accordance with the invention the segmentation is however not performed with respect to the safety region without the region of interest. Instead the region of interest is expanded by a second distance, which is smaller than the first distance, to form an expansion region. The knowledge underlying the invention is that small blood vessels frequently appear on the surface of a lesion, for instance a tumor. Those blood vessels, however, are not relevant to the observations performed in this case and tend instead to cause the person viewing the display to become confused. Due to the region of interest which is defined by the user, possibly also automatically, being expanded to include the second distance, these small blood vessels can be excluded from the detection and segmentation, which also reduces the computation outlay so that they are as a result not visible in the segmentation result and thus in the support display. In this way, the number of blood vessels to be displayed is reduced to exclude blood vessels which are not relevant to the considerations to be performed and the support display is thus clearly improved.

It has incidentally proven to be expedient in this case if the second distance is selected as a quarter up to three quarters of the first distance, for instance as half of the first distance, and/or the first distance is predetermined as 8 to 15 mm, in particular 10 mm and/or as a function of the size of the target area and/or region of interest. Good results have been shown for instance if 10 mm is selected as a first distance, this being a typical safety margin to be selected in the treatment of tumors, and the second distance is determined as half of the first distance, in this case 5 mm. Irrelevant, small blood vessels which frequently appear on the surface of a tumor are thus eliminated during the segmentation, while retaining a sufficiently large search area for blood vessels, which keeps all relevant supply vessels traceable. It should be noted that it may be expedient to select the first distance and/or the second distance as a function of the actual size of the target area or region of interest, in order thus to be able to obtain a larger safety margin particularly with larger target areas/ROI. The values can generally therefore be adjusted in an application-specific manner.

Any methods known in principle in the prior art can be used to segment the blood vessels, wherein it is particularly preferred if in order to segment the blood vessels in a detection region formed by the safety region without the expansion region, blood vessels are detected, whereupon in order to complete the segmentation, a blood vessel connection is sought between the blood vessels detected there and a reference point located outside of the safety region and marking a supply blood vessel supplying the anatomical region including the target area. Detection algorithms can therefore be used for instance, which can identify anatomical structures as blood vessels within the margin located between the first distance and the second distance. Since the anatomical region in which the target area is located is in most cases supplied by a principal supply blood vessel, for instance an artery, from which the treatment typically also takes place by using the medical instrument, the vascular tree is completed as far as a corresponding reference point which marks the supply blood vessel, wherein the method cited in the introduction with respect to the prior art can be used, for instance. For example, the inventive procedure and also the segmentation described herein can be used particularly advantageously in a treatment of a tumor in the liver of a patient. It is known in this case that contrary to other healthy liver tissue, the tumor is supplied arterially, which also typically means that it can be displayed very well in contrast agent recordings. The hepatic artery which supplies the liver has a characteristic shape so that it can also be easily located by automatic detection algorithms, therefore a reference point (often also referred to as a "proximal point") can be established. If connections between the blood vessels detected in the detection region and the hepatic artery are found, the supply vessels can be easily identified.

A particularly advantageous embodiment of the present invention provides that the blood vessels to be shown in the support display are only shown if and to the extent that their course in the safety region approximates the region of interest. Provision can be made in this case for instance, particularly in a region of interest which is selected to be spherical, for the course of the blood vessels to be shown until the normal distance to the region of interest increases. This measure is based on the knowledge that the important piece of information required to assess the blood vessel is that at some point in time it supplies blood to tissue within the safety region. Consequently, the further course of the blood vessel, for instance whether it leaves the safety region once more and enters it again, is a piece of information which is not required for the person undertaking the treatment and is at worst confusing. The display of the blood vessel to be shown is thus shortened to the required, meaningful degree. A significantly more intuitive support display is thus produced. It should be noted that provision can also be made in another embodiment to locate the point of closest proximity of a blood vessel to the region of interest and to show the blood vessel as far as this point of closest proximity, which is then particularly expedient if this information is considered to be relevant to the practitioner.

A further, particularly advantageous embodiment of the present invention results if the blood vessels to be shown in the support display are only shown as far as a bifurcation located within the safety region and/or the further course of only one blood vessel, in particular the largest and/or the blood vessel supplying the region of interest which is produced from the bifurcation, is shown. In this way the display of the blood vessels is limited to the principal supplying blood vessels within the safety region, by the further course being entirely omitted, in order to avoid confusion, if a bifurcation occurs within the safety region, or by only one of the blood vessels, in particular the blood vessel continuing directly to the region of interest, being retained. Other branches are eliminated in the display.

It should be noted that the combination in particular of the three steps of limiting the detection region, omitting blood vessels leading away from the region of interest and treating bifurcations, collectively represents an extremely advantageous filter, which focuses on the actual physical conditions and on the basis of the actual situation and reduces the displays of segmented vessels in the support display to the necessary elements. A visualization is therefore produced, which is adjusted to the requirements of the practitioner by observing the actual conditions. Currently proposed filters, which also consider the size and/or location of the blood vessels, are not adjusted to these requirements and the actual conditions. In particular, combining the three cited steps creates a possibility of displaying complex vascular trees, which contain all the necessary information without being too busy.

In an expedient development of the invention, provision can be made for the courses of the blood vessels to be displayed and to end in the safety region without the expansion region to be traced and extended in the image data record by a path toward the region of interest. The path is preferably selected as a function of the second distance, in particular as corresponding to the second distance. This approach is utilized so that the information relating to the blood vessel course is largely present in the previously excluded expansion region, therefore after filtering the blood vessels and using the already used algorithms, the further course of the blood vessels can also be traced into the expansion region, in particular by using segmentation. The person viewing the display thus identifies that the blood vessels are continued in full as far as the region of interest, since the segmented vessels to be shown are automatically distally traced and displayed from their end, ideally so that they reach the region of interest or extend at least clearly into the expansion region. An extension of the segmentation to include the second distance can be provided, for instance. It is, however, also possible to provide a correction factor, which can focus on the realization actually desired. This expansion of the blood vessels to be shown toward the originally marked region of interest simplifies the check performed by the practitioner on blood vessels which are unintentionally not detected and the support display is more intuitive overall.

It should be noted that it would in principle also be conceivable to select an arbitrary extension in the expansion region, this is however less preferred, particularly since the information relating to the further course of the blood vessels is present in the image data record. In such a less preferred alternative case which is not based on the image data record, the continuation of the blood vessels preferably takes place smoothly, wherein, if necessary, a preferably narrow curve toward the region of interest can be described based on the tangent direction of the previous end of the course.

It should also be noted at this point that due to the target areas which are mostly also poorly identifiable in the image data record, a region of interest marked automatically and/or manually may not contain the entire target area, which is why the safety region is additionally defined. The detection region for relevant blood vessels therefore also relates to the safety region, and not only directly to the surface of the region of interest.

A particularly useful support display is produced if it is created by overlaying the blood vessel courses to be displayed over a slice image derived from the image data record, in particular a Multi-Planar Reconstruction (MPR) image. If the support is to take place during the intervention, it is expedient if the medical instrument, the position of which can be detected for instance by a position determination system, is moreover likewise shown in the support display. It is incidentally also conceivable to base the support display on a current monitoring image, which shows the instrument, for instance a fluoroscopy image. Nonetheless the image data record can be a previously recorded image data record, which then has to be registered with the monitoring image. The image data record is preferably a three-dimensional image data record.

With the objects of the invention in view, there is also provided an apparatus for visually supporting a practitioner with the treatment of a target area of a patient, comprising a receive interface for an image data record which shows the target area and a region of interest defined therein and a safety region, a computing device embodied to perform the method according to the invention and an output interface for the support display. All embodiments relating to the method according to the invention can be transferred analogously to the inventive apparatus, with which the advantages already cited can consequently also be obtained.

In particular, the computing device therefore realizes:
a definition unit for the definition of an expansion region, which surrounds the region of interest at a second distance which is smaller than the first distance,
a segmentation unit for the segmentation of blood vessels in the image data record in a segmentation region including at least the safety region without the expansion region, and
a determination unit for the determination of a support display displaying the blood vessels, in particular together with image data of the image data record and/or the instrument, which can then be forwarded for display on a display apparatus by way of the output interface.

The functional units cited herein can also include subunits, for instance for performing filtering steps to limit the display of the course of blood vessels to be shown. In general the computing device can include hardware components and/or software components, in particular a processor for implementing software components.

With the objects of the invention in view, there is concomitantly provided a computer program which performs the steps of the method according to the invention when it is executed on a computing device. All embodiments relating to the apparatus and the method according to the invention also continue to apply to the computer program, which can be stored on an electronically readable, non-transient data carrier for instance and can thus be loaded into the computing device, in order to realize the method according to the invention there.

It should be noted again that the apparatus according to the invention can also be provided by an imaging device, with which the image data record was recorded, for instance an x-ray device.

Other features which are considered as characteristic for the invention are set forth in the appended claims.

Although the invention is illustrated and described herein as embodied in a method, an apparatus and a computer program for visually supporting a practitioner with the treatment of a target area of a patient, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
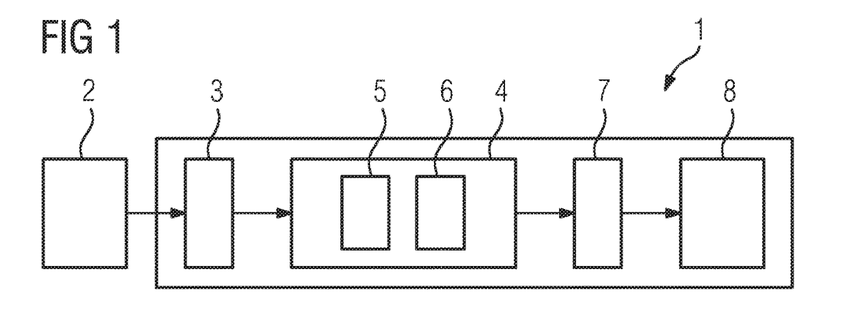
FIG. 1 is a block diagram of a support apparatus according to the invention.

Referring now to the figures of the drawings in detail and first, particularly, to FIG. 1 thereof, there is seen a block diagram of an apparatus 1 according to the invention for supporting a practitioner with the planning and/or performance of a treatment in a target area, for instance a tumor within the liver. The treatment should take place in this case by a treatment agent being given by using a medical instrument in a supply vessel. The treatment agent is transported through the supply vessel to the target area and acts locally there. One example of treatments which can be supported by the method according to the invention and the apparatus 1 is TACE treatment (Transarterial chemoembolization). The support apparatus 1 can be integrated into an imaging device 2 or can obtain an image data record of the target area, for instance an x-ray image data record, directly or indirectly therefrom, in which before starting the method according to the invention, a region of interest, which describes the target area, was already marked automatically and/or manually, as a result of which a safety region was automatically defined at a first distance about the region of interest so that a safety margin is formed. This marking can also take place on the support apparatus 1.

A receive interface 3 receives the image data record and the input data describing the region of interest and the safety region. A computing device 4, which includes a processor 5 and a storage device 6 in this case, is embodied to perform the method according to the invention, which is discussed with more precise details below. In particular, to conclude the method according to the invention, a support display is determined and is forwarded through an output interface 7 to be shown on a display apparatus 8, which forms part of the support apparatus in this case.

Figure 2:
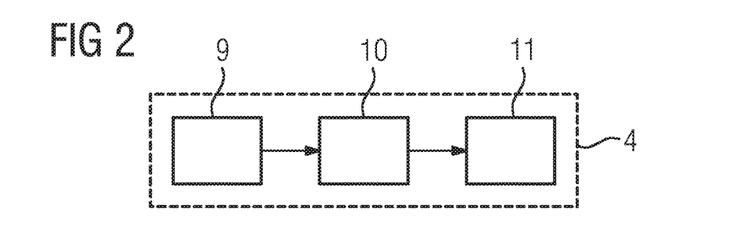
FIG. 2 is a block diagram showing functional units of a computing device of the apparatus according to FIG. 1.

FIG. 2 shows the functional embodiment of the computing device 4. This firstly includes a definition unit 9 for the definition of an expansion region, which surrounds the region of interest at a second distance, which is smaller than the first distance (and thus does not correspond thereto), a segmentation unit 10 for the segmentation of blood vessels in the image data record in a segmentation region including at least the safety region without the expansion region and a determination unit 11 for the determination of a support display displaying the blood vessels, at present collectively with image data of the image data record and, if support is provided at the time of the intervention, the instrument. The support display is then forwarded through the output interface 7 to the display apparatus 8 and output by using suitable control commands of the determination unit 11.

Figure 3:
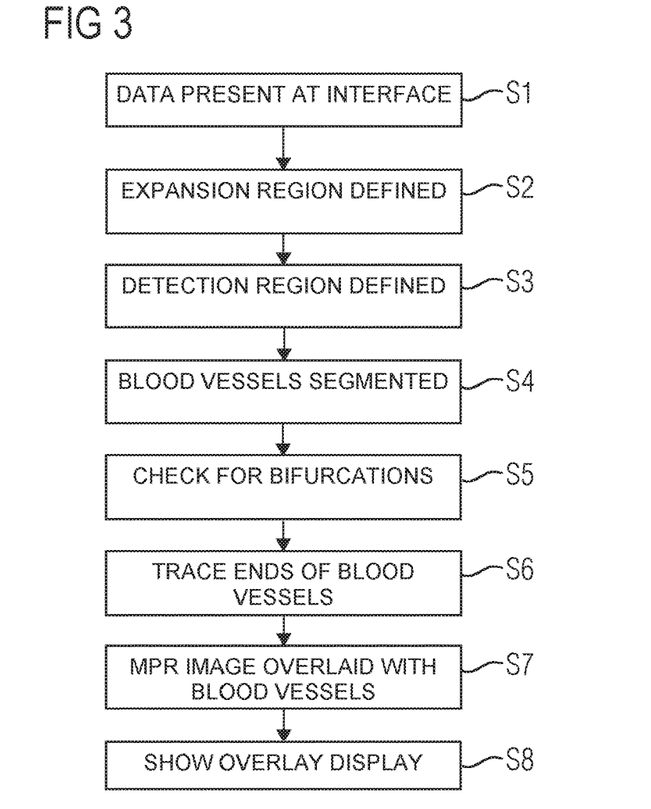
FIG. 3 is a flow chart of an exemplary embodiment of the method according to the invention.
Figure 4:
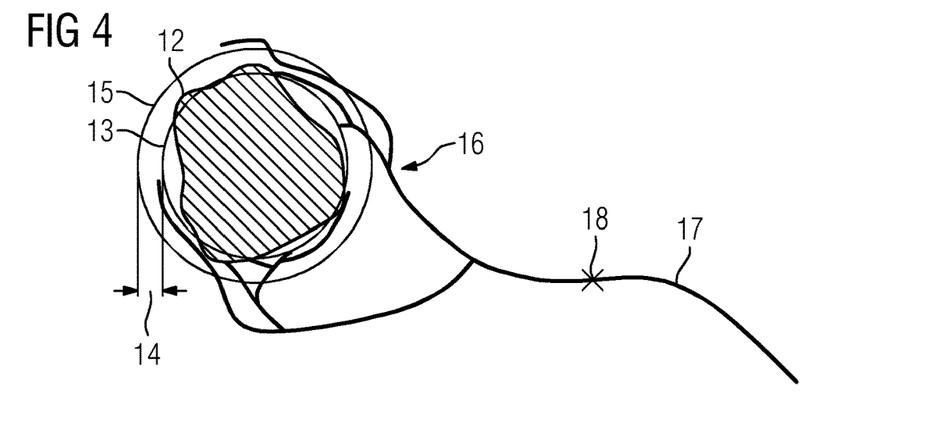
FIGS. 4-8 are diagrammatic, cross-sectional views showing displays of a target area and surrounding blood vessels which are used to explain the method according to the invention.

A more precise explanation will be provided below on the basis of the flow chart, shown in FIG. 3, of an exemplary embodiment of the method according to the invention together with the diagrammatic representations in FIGS. 4 to 8, which illustrate different measures to improve the support display. By way of example FIG. 4 shows the underlying method. A target area 12, which can at least for the most part be identified in the image data record, is described in its position by a region of interest 13, which is currently defined to be spherical in the three-dimensional image data record and is surrounded at a first distance 14 from the boundary of a safety region 15. Clearly, parts of the target area 12 are not determined in the region of interest 13, since they were for instance not identifiable in the image data record but are however located within the safety region 15.

A plurality of blood vessels 16 are also shown, which supply the target area 12 or at least tissue within the target region 15. All of these blood vessels 16 are connected to a supply blood vessel 17 for the anatomical region in which the target area 12 is located, which is a hepatic tumor to the hepatic artery in the example shown.

In the prior art, blood vessels 16 would now be sought in a detection region, which includes the safety region 15 without the region of interest 13 whereupon, by using suitable algorithms, connections to the supply blood vessel 17, distinguished by a reference point 18, are located. If a display was produced therefrom, a confusing image would be produced for the practitioner, since it would contain small vessels 16 close to the target area 12 as well as irrelevant branches and blood vessels 16 that depart from the safety region 15 again.

The filter generated by using the method according to the invention should be of assistance in this respect. It is assumed in this case in a step S1 of the method according to the invention that the image data record and the data describing the region of interest 13 and the safety region 15 are present at the receive interface 3. An expansion region is then defined in a step S2, which is performed by the definition unit 9. The expansion region surrounds the region of interest 13 at a second distance which is smaller than the first distance, wherein the second distance is currently selected to be half as large as the first distance. This is shown in more detail by FIG. 5 which, in addition to the region of interest 13 and the safety region 15, also shows an expansion region 20 provided at a second distance 19 from the region of interest 13.

Figure 5:
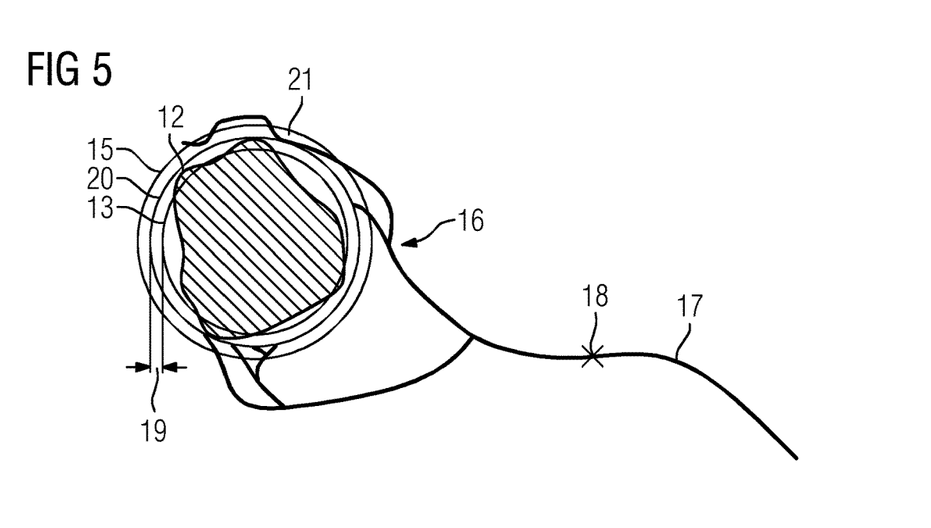

The expansion region 20 is used in a step S3, which is performed by the segmentation unit 10, to define a detection region 21, which is currently formed by the safety region 15 without the expansion region 20.

Blood vessels 16 are only sought in this restricted detection region in step S3, for which purpose algorithms known in the prior art can be used. Accordingly, the blood vessels located within the second distance 19 about the region of interest 13 are also no longer shown in FIG. 5. They are no longer segmented and can therefore also not be contained in the support display that is ultimately produced, which excludes in particular the plurality of small blood vessels 16, which frequently appear directly adjacent to target vessel 12.

Similarly in step S4, in order to complete the segmentation of the vascular tree formed by the blood vessels 16, for each of the detected blood vessels 16, a connection to the reference point 18 is sought, as is known in principle.

The following steps for determining the support display are performed by the determination unit 11. In principle, the blood vessels 16 which are segmented in the preceding segmentation step S4 are now the blood vessels to be shown, however the display of the course of these blood vessels is limited further in accordance with the invention. To this end, firstly blood vessels 16 again leading away from the region of interest 13 within the safety region 15 are no longer included in the support display, as soon as their distance from the region of interest 13, in this case the normal distance, increases again. This is explained in more detail by FIG. 6, as can be clearly identified for instance in a region 22. The course of the blood vessel 16, even temporarily departing again from the safety region 15, is only shown until it reaches the shortest distance from the region of interest 13.

Figure 6:
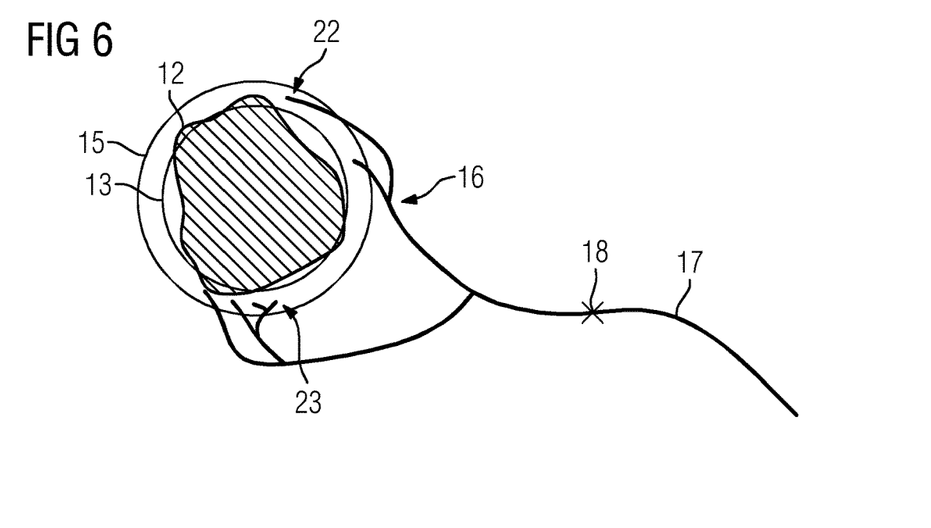
Figure 7:
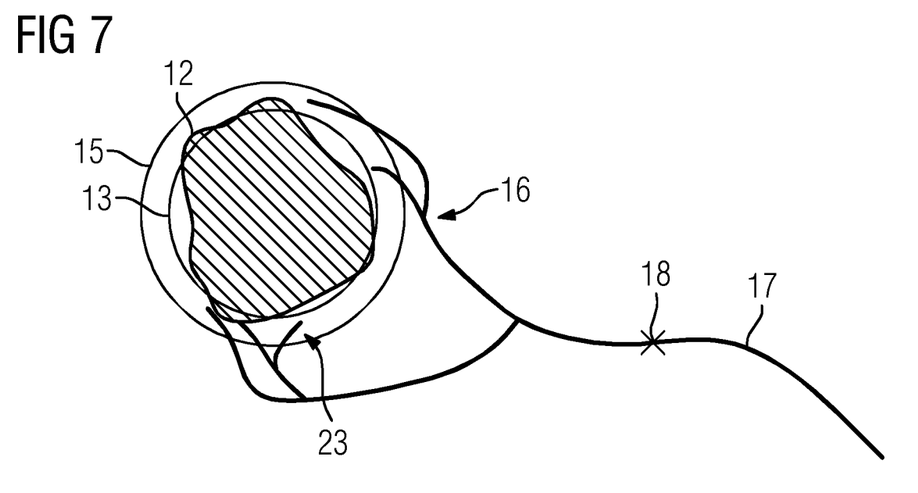

In a further step S5, a check of the blood vessels 16 is performed to determine whether bifurcations occur within the safety region 15, such as is the case for instance in the blood vessel in a region 23 shown in FIG. 6. With bifurcations of this type, the blood vessel emerging from the bifurcation which supplies the region of interest 13 most directly is shown again. This is clearly apparent in the region 23 in FIG. 7 in comparison with FIG. 6.

Figure 8:
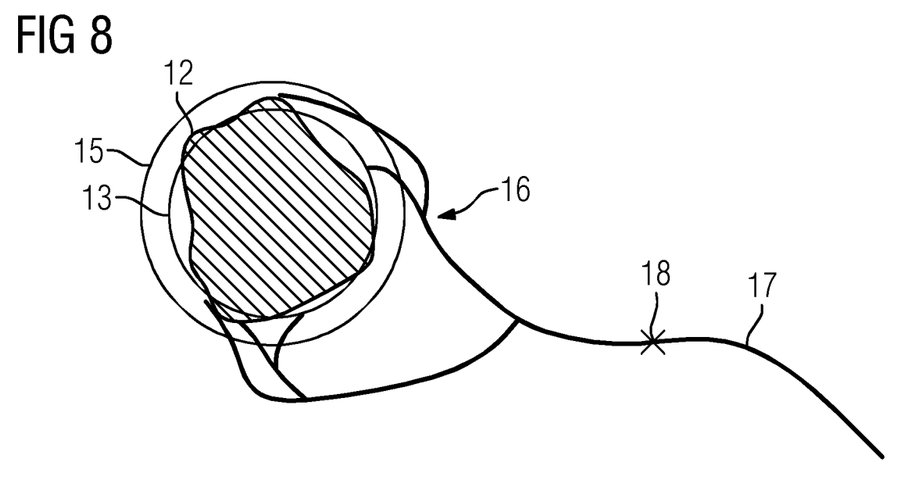

In a further step S6, the illustrated ends of the blood vessels 16 are now traced in the safety region 15 toward the region of interest 13 about a path in the image data record and are continued in the display, which can correspond to the second distance 19 for instance, but may also be somewhat smaller or larger than this value, ideally in such a way that they appear to proceed as far as the region of interest, in particular a lesion. This is shown diagrammatically in FIG. 8. If the displays in FIG. 4 and FIG. 8 are now compared, it is immediately apparent that it is still only the important blood vessels 16 which are relevant to the practitioner that are visible. Those blood vessels moreover have for the most part been segmented as far as the region of interest 13. It should be noted that if it is established during tracing that the anatomical object described by the region of interest, for instance a tumor, has been reached, tracing can naturally be stopped.

In a step S7, the blood vessels 16 to be displayed that were treated according to steps S4 to S6 are now overlaid over an MPR image of the image data record, so that the overlay display is produced, which is finally shown in step S8 on the display apparatus 8, and serves to improve the virtual support of the person undertaking the treatment.

Although the invention has been illustrated and described in greater detail by the preferred exemplary embodiment, the invention is not limited by the examples disclosed and the person skilled in the art will be able to derive other variations on this basis without moving beyond the scope of protection of the invention.

The invention claimed is:

1. A method for visually supporting a practitioner with the treatment of a target area or a tumor of a patient by using a treatment agent to be introduced into the target area through at least one supply blood vessel by using a medical instrument, the method comprising the following steps:
   obtaining an image data record from an imaging device;
   defining a region of interest describing the target area and a safety region surrounding the region of interest at a first distance, in an image data record showing the target area;
   subsequently defining, with a computing device including a processor, an expansion region surrounding the region of interest at a second distance being smaller than the first distance;
   segmenting, with the computing device, blood vessels in the image data record in a segmentation region including the safety region, but not segmenting blood vessels in the image data record in the expansion region; and
   displaying, on a display device receiving data from the computing device, a support display image displaying the segmented blood vessels overlaid over an image of the image data record.

2. The method according to claim 1, which further comprises carrying out the step of displaying the support display image displaying the blood vessels together with image data of the medical instrument.

3. The method according to claim 1, which further comprises:
   detecting blood vessels for segmenting the blood vessels in a detection region formed by the safety region without the expansion region; and
   completing the segmentation by seeking a blood vessel connection between the detected blood vessels and a reference point located outside of the safety region and marking a supply blood vessel supplying an anatomical region including the target area.

4. The method according to claim 1, which further comprises selecting the second distance to be between one quarter and three quarters of the first distance.

5. The method according to claim 1, which further comprises predetermining the first distance to be between 8 mm and 15 mm, or 10 mm, or a function of a size of at least one of the target area or the region of interest.

6. The method according to claim 1, which further comprises showing the blood vessels in the support display only if their course in the safety region approximates the region of interest.

7. The method according to claim 6, which further comprises showing the course of the blood vessels until a distance to the region of interest increases beyond a predefined amount.

8. The method according to claim 7, wherein the region of interest is spherical.

9. The method according to claim 1, which further comprises showing the blood vessels in the support display only as far as at least one of a bifurcation located within the safety region or a further course of only one of the blood vessels or a largest blood vessel emerging from the bifurcation is shown.

10. The method according to claim 9, wherein the one blood vessel is a blood vessel supplying the region of interest.

11. The method according to claim 1, which further comprises tracing courses of the blood vessels to be displayed and ending in the safety region without the expansion region about a path toward the region of interest in the image data record, and showing the courses in an extended manner.

12. The method according to claim 11, wherein the path is selected as a function of the second distance.

13. The method according to claim 11, wherein the length of the path traced corresponds to the second distance.

14. The method according to claim 1, wherein the image of the image data record is a slice image derived from the image data record.

15. The method according to claim 14, wherein the slice image is a Multi-Planar Reconstruction (MPR) image.

16. An apparatus for visually supporting a practitioner with the treatment of a target area or a tumor of a patient by using a treatment agent to be introduced into the target area through at least one supply blood vessel by using a medical instrument, the apparatus comprising:
   an imaging device configured to provide an image data record showing the target area;
   an interface configured to receive the image data record showing the target area, a region of interest defined in the target area and a safety region;
   a computing device including a processor, said computing device configured to receive the image data record from the interface and perform the following steps:

defining the region of interest describing the target area and the safety region surrounding the region of interest at a first distance, in the image data record showing the target area;

subsequently defining an expansion region surrounding the region of interest at a second distance being smaller than the first distance;

segmenting blood vessels in the image data record in a segmentation region including the safety region, but not segmenting blood vessels in the image data record in the expansion region; and an output interface connected to receive data from said computing device and provide a support display image to a display device displaying the segmented blood vessels overlaid over an image of the image data record.

17. A non-transitory computer readable medium with computer executable instructions stored thereon executed by a processor to perform a method for visually supporting a practitioner with the treatment of a target area or a tumor of a patient by using a treatment agent to be introduced into the target area through at least one supply blood vessel by using a medical instrument, the method comprising the following steps:

obtaining an image data record from an imaging device;

defining a region of interest describing the target area and a safety region surrounding the region of interest at a first distance, in an image data record showing the target area;

subsequently defining, with the computing device including the processor, an expansion region surrounding the region of interest at a second distance being smaller than the first distance;

segmenting, with the computing device, blood vessels in the image data record in a segmentation region including the safety region, but not segmenting blood vessels in the image data record in the expansion region; and displaying, on a display device receiving data from the computing device, a support display image displaying the segmented blood vessels overlaid over an image of the image data record.

* * * * *